United States Patent [19]

Sarantakis

[11] 4,185,010
[45] Jan. 22, 1980

[54] NONAPEPTIDES

[75] Inventor: Dimitrios Sarantakis, West Chester, Pa.

[73] Assignee: American Home Products Corporation, New York, N.Y.

[21] Appl. No.: 968,708

[22] Filed: Dec. 12, 1978

[51] Int. Cl.$^2$ ..................... C07C 103/52; A61K 37/00
[52] U.S. Cl. .............................. 260/112.5 S; 424/177
[58] Field of Search .................. 260/112.5 S; 424/177

[56] References Cited

U.S. PATENT DOCUMENTS 4,105,603  8/1978  Vale, Jr. et al. ................ 260/112.5 S Primary Examiner—Delbert R. Phillips
Attorney, Agent, or Firm—Richard K. Jackson

[57] ABSTRACT (des-Ala$^1$, Gly$^2$, Asn$^5$, Thr$^{12}$, Ser$^{13}$)-His$^4$-D-Trp$^8$-Abu$^{10}$-Somatostatin and analogues thereof selectively inhibit glucagon release without materially altering blood serum growth hormone and insulin levels.

4 Claims, No Drawings

NONAPEPTIDES

SUMMARY OF THE INVENTION (des-Ala[1], Gly[2], Asn[5], Thr[12], Ser[13])-His[4]-D-Trp[8]-Abu[10]-Somatostatin and analogues thereof selectively inhibit glucagon release without materially altering blood serum, growth hormone and insulin levels.

DETAILED DESCRIPTION OF THE INVENTION

In accordance with this invention there is provided a novel group of nonapeptides of formula I:

in which
the A groups are hydrogen or a direct bond between the two sulfur atoms;
X is hydrogen or $NH_2$;
$X_1$ is L-Trp or D-Trp;
$X_2$ is L-Abu, L-Val, L-Phe or L-Thr;
and the two cysteinyl moieties are of L- or D- configuration, the linear precursor intermediates or pharmaceuticaly acceptable salts thereof.

In the depicted formula and throughout this specification and claims, where the chirality of an amino acid is not indicated or otherwise stated, it is understood to be of the L-series.

The linear precursor intermediates, which comprise an additional aspect of the invention may be depicted as follows in formula II:

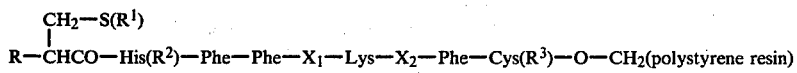

in which
R is hydrogen or a protected α-amino group;
$R^1$ is a sulfhydryl protecting group;
$R^2$ is an amino protecting group;
$X_1$ is L-Trp or D-Trp;
$X_2$ is L-Abu, L-Val, L-Phe, or L-Thr;
$R^3$ is a sulfhydryl protecting group;
and the two cysteinyl moieties are of L- or D- configuration.

These intermediates comprise the fully protected nonapeptide bound to a hydroxymethylated polystyrene resin support employed in solid phase synthesis of the polypeptide.

The pharmaceutically acceptable salts of the compounds (I) of this invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic or ascorbic acid and the like. Acetic acid is the preferred acid.

The nonapeptides I selectively inhibit release of glucagon without materially altering blood levels of growth hormone or insulin. As such, they are useful in treatment of hyperglycemia in general and specifically in diabetes mellitus which is characterized by excessive glucagon secretion and deficient insulin release. Thus, for example, the postprandial hyperglycemic state in insulin-dependent diabetes may be improved through suppression of excessive glucagon by administration of the compounds of this invention with or without concomitant administration of suboptimal amounts of exogenous insulin. Likewise, the compounds of this invention are useful in the treatment of glucagon secretion by benign and malignant islet-cell tumors to obtain the normoglycemic state.

The protecting groups employed during preparation of the intermediate of Formula II are conventional in solid phase polypeptide synthesis. Thus, in the above formula, the protecting group embraced in the definition of R may be formyl, trifluoroacetyl, phthalyl, p-chlorobenzyloxycarbonyl, p-nitrobenzyloxycarbonyl, tert-butyloxycarbonyl (Boc), 2,2,2-tri-chloroethoxycarbonyl, amyloxycarbonyl, cyclopentyloxycarbonyl, cylcohexyloxycarbonyl, trityl, etc., the preferred group being tert-butyloxycarbonyl.

Examples of the sulfhydryl protecting groups $R^1$ and $R^3$ and the hydroxyl group of threonyl are benzyl, p-methoxybenzyl, p-chlorobenzyl, p-nitrobenzyl, trityl, benzyloxycarbonyl, p-methoxybenzyloxycarbonyl, and the like. The p-methoxybenzyl group is preferred for protection of cysteinyl sulfur while the benzyl group is preferred for the threonyl moiety $X_2$.

Protecting groups for the imidazole nitrogen (im) atom of histidine include tosyl, benzyloxycarbonyl, and tert-butyloxycarbonyl, preferably the tosyl group.

The support employed in the solid phase synthesis of these compounds is a chloromethylated or hydroxymethylated polystyrene resin cross-linked with divinylbenzene. These resins are prepared by known methods and are commercially available in the art.

The following examples illustrate the preparation of (des-Ala[1], Gly[2], Asn[5], Thr[12], Ser[13])-His[4]-D-Trp[8]-Abu[10]-somatostatin, which is representative, in its solid phase preparation and biological activity, of the other compounds of formula I, supra.

EXAMPLE 1 tert-Butyloxycarbonyl-S-p-methoxybenzyl-L-cysteinyl-im-tosyl-L-histidyl-L-phenylalanyl-L-phenylalanyl-D-tryptophyl-L-lysyl-L-α-aminobutyryl-L-phenylalanyl-S-methoxybenzyl-L-cysteinyl hydroxymethyl polystyrene ester Chloromethylated polystyrene resin (Lab Systems, Inc.) 1% cross-linked with divinylbenzene was esterified with Boc-Cys(SMBzl)-OH according to Gisin *Helv. Chim. Acta.* 56 1976(1973). The polystyrene resin ester was treated according to Schedule A for the incorporation of Boc-Phe-OH, Boc-Abu-OH(L-α-aminobutyric acid), Boc-Lys(ClCbz)-OH, Boc-D-Trp-OH, Boc-Phe-OH, Boc-Phe-OH, Boc-His(Tos)-OH and Boc-Cys(SMBzl)-OH to afford the title peptidoresin.

Schedule A

1. Wash with $CH_2Cl_2 \times 3$
2. Treat with TFA-$CH_2Cl_2$-EDT(1:1:5%, v/v) for 5 min.
3. Treat as in 2 for 25 min.
4. Wash with $CH_2Cl_2 \times 3$
5. Wash with DMF
6. Treat with 12% TEA in DMF twice for 3 min.

7. Wash with DMF
8. Wash with $CH_2Cl_2 \times 3$
9. Treat with 4 equivalents of the corresponding amino acid derivative in $CH_2Cl_2$-DMF and stir for 5 min.
10. Add in two portions 5 equivalents of DIC dissolved in $CH_2Cl_2$ and over a period of 30 min. Reaction time 6 hours.
11. Wash with DMF$\times 3$.
12. Wash with $CH_2Cl_2 \times 3$
13. Test ninhydrin reaction according to Kaiser et al., Annal. Biochem. 34, 595 (1970). In case of incomplete reaction repeat lines 9 to 13 as above.

EXAMPLE 2

L-Cysteinyl-L-histidyl-L-phenylalanyl-L-phenylalanyl-D-tryptophyl-L-lysyl-L-α-aminobutyryl-L-phenylalanyl-L-cysteine cyclic (1-9) disulfide The peptidoresin of the previous example (13 g.) was mixed with anisole (26 ml.) and treated with liquid HF in an ice-bath for 60 minutes and with exclusion of air. The excess liquid HF was removed under vacuo and the residue was taken in 2M-aq. acetic acid. The mixture was filtered and the filtrate was diluted with water to 5 liters. The pH was adjusted to 7 with dilute $NH_4OH$ and the disulfhydryl peptide was oxidized with $K_3Fe(CN)_6$ to cyclic disulfide. The pH of the mixture was adjusted to 5 with glacial acetic acid and treated with Bio Rad AG 3 (chloride form) then the peptidic material was absorbed onto Bio Rex 70 (H+ form) and eluted with a mixture of pyridineglacial acetic acid-water (30:4:66). The fractions containing peptidic material were pooled and lyophilized to yield 818 mg. of crude product.

The above crude product was applied onto a column (2.5×150 cm) of Sephadex G25 and eluted with 10% aq. acetic acid. The material which emerged in fractions (5.1 ml. each) 117 to 153 was pooled and lyophilized to yield 397 mg. of material. This material was applied onto a column (2.5×20.cm) of carboxymethyl cellulose CM 52 and eluted with a linear gradient of, water to 0.6 of ammonium acetate. The material which emerged in fractions (3.3 ml each) 55 to 90 was pooled and lyophilized to yield 91 mg. of the title nonapeptide. TLC, precoated glass plates Avicel, chlorox spray. $R_f$(BWA, 4:1:1) 0.50, $R_f$(BWA, 4:5:1) 0.42, $R_f$(t-A.P.W., 7:7:6) 0.76. Amino acid analysis: Cys (2) 1.73; Phe (3) 3; Lys (1) 1.16; His (1) 1.16; Trp (1) 1.03; Abu, present, factor not available.

Electrophoresis, 500 v, Avicel precoated glass plates, 45 minutes, pH 6.8, one spot 3.6 cm towards negative pole.

The product of the preceding examples illustrate the selective activity of the compounds of formula I for glucagon suppression in the following standard procedure:

Albino male rate are administered Nembutal intraperitoneally at a dose of 50 milligrams per kilogram. Fifteen minutes later a subcutaneous injection of the test compound or physiological saline (control) is administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot is assayed for growth hormone (GH), insulin, and glucagon by radioimmunoassay. The results of the assay are as follows:

| Compound | Dose μg/kg | GH ng/ml | INS μU/ml | GLUN pg/ml |
|---|---|---|---|---|
| Control | — | 454 ± 106 | 269 ± 37 | 60 ± 10 |
| Example 2 | 1,000 | 413 ± 98 | 262 ± 39 | 31 ± 5+ |

+p<0.05

As with administration of any therapeutic agent used in the treatment of diabetes mellitus, the compounds of this invention must be individualized for the patient under guidance and close control of the attending physician to reach optimism blood levels of insulin and glucagon. Doses for achieving the desired state vary with the condition of the patient, such as age, amount of endogenous insulin produced, the presence of glucagon secretincy tumors, the route of administration, the duration of treatment, severity of the condition being treated, etc.

Thus, the compounds of formula I may be administered alone or in combination with insulin with or without carriers or excipients conventional to the route of administration selected, which may be oral, intravenous, subcutaneous, intramuscular, intranasal, intrarectally, etc. Suitable pharmaceutical compositions for each application are apparent to those skilled in the art.

What is claimed is:

1. A common of the formula:

in which
the A groups are hydrogen or a direct bond between the two sulfur atoms;
X is hydrogen or $Nh_2$;
$X_1$ is L-Trp or D-Trp;
$X_2$ is L-Abu, L-Val, L-Phe or L-Thr;
and the two cysteinyl moieties are of L- or D-configuration, the linear precursor intermediates or pharmaceutically acceptable salts thereof.

2. A compound of claim 1 which is L-Cys-LHis-L-Phe-L-Phe-D-Trp-L-Lys-L-Abu-L-Phe-L-Cys cyclic (1-9) disulfide or a pharmaceutically acceptable salt thereof.

3. A compound of the formula:

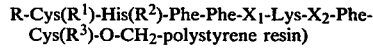

in which
R is an α-amino protecting group;
$R^1$ is a sulfhydryl protecting group;
$R^2$ is amino protecting group;
$X_1$ is L-Trp or D-Trp;
$X_2$ is L-Abu, L-Val, L-Phe or L-Thr($R^4$) where $R^4$ is a hydroxyl protecting group;
$R^3$ is a sulfhydryl protecting group;
and the two cysteinyl moieties are of L- or D- configuration.

4. A compound of claim 3 in which R is t-butyloxycarbonyl; $R^1$ is p-methoxybenzyl; $R^2$ is tosyl; $X_1$ is D-Trp; $X_2$ is α-aminobutyryl and $R^3$ is p-methoxybenzyl.

UNITED STATES PATENT OFFICE
CERTIFICATE OF CORRECTION

Patent No. 4,185,010          Dated January 22, 1980

Inventor(s) Dimitrios Sarantakis

It is certified that error appears in the above-identified patent and that said Letters Patent are hereby corrected as shown below:

Column 1, line 17, in the structural formula, after "Lys", insert -- $-X_2-$ --;

Column 4, line 30, Claim 1, delete "common" and insert -- compound --;

line 33, in the structural formula after "Lys", insert -- $-X_2-$ --;

line 38, delete "$Nh_2$" and insert -- $NH_2$ --.

Signed and Sealed this

Seventeenth Day of June 1980

[SEAL]

Attest:

SIDNEY A. DIAMOND

Attesting Officer      Commissioner of Patents and Trademarks